United States Patent

Safaev et al.

[11] 4,287,344
[45] Sep. 1, 1981

[54] N,N-BIS-(DECAHYDROQUINOLYL-N-METHYL)IMIDAZOLIN-2-THIONES

[76] Inventors: Abidzhan Safaev, "P" Ts-1, 26-a, kv. 28; Abduvasit Kadyrov, ulitsa Vavilova, 11; Zhakhongir G. Saidaliev, ulitsa 1 Sputnik, 7; Tulyagan F. Faiziev, ulitsa Almazar, Shelkomotalny proezd, 31-a, all of Tashkent, U.S.S.R.

[21] Appl. No.: 821,560

[22] Filed: Aug. 3, 1977

[51] Int. Cl.³ .................................. C07D 401/14
[52] U.S. Cl. .................................................. 546/164
[58] Field of Search ............... 260/283 S, 283 BI; 548/318, 317; 546/164

[56] References Cited

U.S. PATENT DOCUMENTS

| | | | |
|---|---|---|---|
| 2,118,244 | 5/1938 | Jensch | 260/283 BI |
| 2,189,717 | 2/1940 | Scott | 260/283 BI |
| 2,228,166 | 1/1941 | Jensch | 260/283 BI |
| 2,700,028 | 1/1955 | Jarboe | 548/317 |
| 3,932,452 | 1/1976 | Schwen et al. | 548/317 |

FOREIGN PATENT DOCUMENTS 575114 4/1933 Fed. Rep. of Germany.
1535143 12/1978 United Kingdom.

OTHER PUBLICATIONS

Criegee et al., Chem. Berichte, 89, pp. 870-876.
Chem. Abstracts, vol. 82, 1975, p. 502, Safaev et al., Abst. 16832b (USSR Pat. 442,184, 5 Sep. 1974).
Stavrovskaya et al., "Organic Chemistry Journal", 30,689 (1960).
March, Advanced Org. Chem., (1968), p. 424.
Morrison et al., Org. Chem. (1966), p. 740.

Primary Examiner—Donald G. Daus
Assistant Examiner—W. B. Springer
Attorney, Agent, or Firm—Lackenbach, Lilling & Siegel

[57] ABSTRACT

The present invention relates to novel derivatives of imidazolin-2-thione and a method of preparing same. These novel compounds comprise N,N'-bis-substituted imidazolin-2-thiones of the formula:

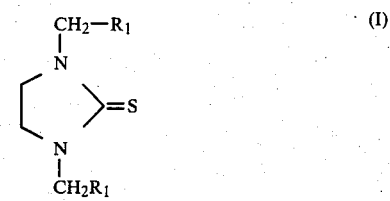

wherein $R_1$ is

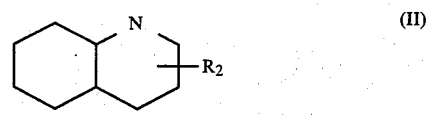

$R_2$ is hydrogen or methyl.

The method of preparing said compounds according to the present invention comprises reacting imidazolin-2-thione with formaldehyde and a compound of the formula:

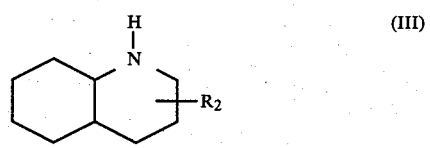

wherein $R_2$ is hydrogen or methyl, at the molar ratio therebetween of 1:2:2 respectively in an aqueous medium or in a medium of polar organic solvents at a temperature ranging from 20° to 80° C. The method according to the invention makes it possible to obtain the desired product at a high yield (up to 93% of the theoretical value). The products may be widely employed in the rubber industry as efficient accelerators for vulcanization of rubber mixes (vulcanization time is 10–15 minutes), as corrosion inhibitors for non-ferrous metals, as flotation reagents for extraction of non-ferrous metals from waste waters and as herbicides and insecticides in agriculture.

6 Claims, No Drawings

N,N-BIS-(DECAHYDROQUINOLYL-N-METHYL-)IMIDAZOLIN-2-THIONES

The present invention relates to novel derivatives of imidazolin-2-thione and to a method of preparing same.

In accordance with the present invention, novel derivatives of imidazolin-2-thione comprise N,N'-bis-substituted imidazolin-2-thione of the formula:

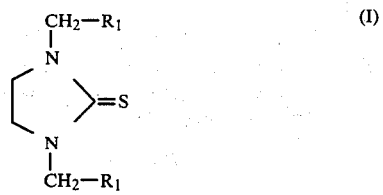

wherein $R_1$ is

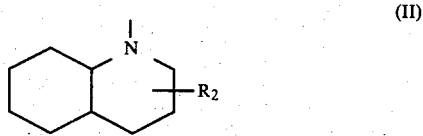

$R_2$ is hydrogen or methyl.

The compounds of the present invention may be useful in the rubber industry as highly-effective vulcanization accelerators for different rubber mixes based on synthetic and natural rubbers (for example, isoprene, chloroprene, butadiene-nitrile rubbers). Therewith, vulcanization time is only 10–15 minutes, i.e. by 2–3 times less than the vulcanization time obtained when the use of conventional compounds such as imidazolin-2-thione and decahydroquinolyl-N-thiol.

Furthermore, novel derivatives of imidazolin-2-thione according to the present invention may be used as corrosion inhibitors for non-ferrous metals, as flotoreagents in the extraction of non-ferrous metals from waste waters, as herbicides and insecticides in agriculture.

The method of preparing novel compounds of formula (I) according to the present invention resides in that imidazolin-2-thione is reacted with formaldehyde and a compound of the formula:

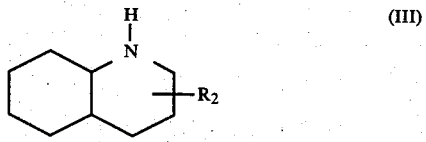

wherein $R_2$ is hydrogen or methyl, at the molar ratio of the components equal to 1:2:2 respectively in an aqueous medium or in a medium of polar organic solvents at a temperature ranging from 20° to 80° C., preferably from 50° to 60° C.

The method according to the present invention makes it possible to obtain the desired products with a high yield thereof (up to 93% of the theoretical value).

In the method according to the present invention the interaction of the starting reactants is effected in a single reactor, whereby the process of producing the desired compounds becomes substantially simplified.

In the method of the present invention, as the compounds of formula (III) use is made of, for example, decahydroquinoline, 2-methyl-, 3-methyl-, 4-methyl, 6-methyl- or 8-methyl- decahydroquinoline.

As the polar organic solvents in the method according to the present invention use may be made of, for example, ethanol dioxane, chloroform, benzene.

For a better understanding of the present invention, the following Examples illustrating preparation of N,N-bis-substituted imidazolin-2-thiones of the formula (I) are given herein below.

EXAMPLE 1

N,N'-bis-(decahydroquinolino-N-methyl)-imidazolin-2-thione

Into a three-neck flask provided with a reflux condenser and a mechanical stirrer there are charged 2.45 g (0.025 mol) of imidazolin-2-thione, 10 ml of ethanol (solvent), 6.96 g (0.05 mol) of decahydroquinoline and 1.5 g (0.05 mol) of formaldehyde. Thereafter, the reaction mixture is heated to a temperature within the range of from 50° to 60° C. and maintained at this temperature for a period of 1.5–2 hours. On expiration of this time, the solvent is evaporated to give a solid substance as a residue. The resulting product is further washed with water to remove the unreacted imidazolin-2-thione recrystallized from benzene and dried. The desired product yield is 9.3 g or 92.7% of the theoretical value.

The thus-prepared compound melts at 127°–128° C. It is soluble in ethanol, chloroform, benzene, dioxane, hot acetone. It is insoluble in distilled water. Elemental analysis data for $C_{23}H_{40}N_4 S$ are as follows:

Found, %: C 68.24; H 10.01; N 13.93; S 7.45; C 68.44; H 9.92; N 14.05. Calculated, %: C 68.31 H 9.90 N 13.86 S 7.82.

EXAMPLE 2

N,N'-bis-(2-methyldecahydroquinolino-N-methyl)-imidazolin-2-thione

Under conditions similar to those described in Example 1, reacted are 2.45 g (0.025 mol) of imidazolin-2-thione with 7.65 g (0.05 mol) of 2-methyldecahydroquinoline and 15 g (0.05 mol) of formaldehyde. The reaction time is 2–2.5 hours. The resulting thick mass is reprecipitated from diethyl ether and dried. The desired product yield is 7.27 g or 79.5% of the theoretical value.

The thus-prepared compound melts at 111°–112° C. It is soluble in benzene, acetone, dioxane, chloroform, carbon tetrachloride and dichloroethane.

The resulting compound is insoluble in water, ethanol, diethyl ether. The data of elemental analysis for $C_{25}H_{46}N_4S$ are as follows:

Found, %: C 70.12; H 10.41; N 12.68; S 7.71; C 69.84; H 10.83; N 12.48. Calculated, %: C 69.14 H 10.59 N 12.98 S 7.3.

EXAMPLE 3

N,N'-bis-(6-methyldecahydroquinolino-N-methyl)-2-thione

Under conditions similar to those described in the foregoing Example 1 reacted are 2.45 g (0.025 mol) of imidazolin-2-thione with 7.65 g (0.05 mol) of 6-methyl-decahydroquinoline and 1.5 g (0.05 mol) of formaldehyde. The reaction temperature is 35°–40° C., duration 1–1.5 hours. The desired product yield is 7.72 g which corresponds to 84.5% of the theoretical value.

EXAMPLE 4

N,N'-bis-(8-methyldecahydroquinolino-N-methyl)-imidazolin-2-thione

Under conditions similar to those described in Example 1 hereinbefore reacted are 2.45 g (0.025 mol) of imidazolin-2-thione with 7.65 g (0.05 mol) of 8-methyldecahydroquinoline and 1.5 g (0.05 mol) of formaldehyde. The reaction temperature is 35°–40° C., duration 2–2.5 hours. The desired product yield is 7.59 g which corresponds to 83% of the theoretical value.

The thus-prepared compound melts at 224°–225° C. It is soluble in the above-mentioned organic solvents.

EXAMPLE 5

N,N'-bis-(decahydroquinolino-N-methyl)-imidazolin-2-thione

Under conditions similar to those described in the foregoing Example 1 reacted are 2.45 g (0.025 mol) of imidazolin-2-thione with 6.96 g (0.05 mol) of decahydroquinoline and 1.5 g (0.05 mol) of formaldehyde. The desired product yield is 7.82 g which corresponds to 78% of the theoretical value.

EXAMPLE 6

N,N'-bis-(decahydroquinolino-N-methyl)-imidazolin-2-thione

Under conditions similar to those described in the foregoing Example 1 there are reacted 2.45 g (0.025 mol) of imidazolin-2-thione with 6.96 g (0.05 mol) of decahydroquinoline and 1.5 g (0.05 mol) of formaldehyde. The reaction temperature is 40° C.; duration—1.5–2 hours. The desired product yield is 8.63 g which corresponds to 85% of the theoretical value.

EXAMPLE 7

N,N'-bis-(decahydroquinolino-N-methyl)-imidazolin-2-thione

Under conditions similar to those described in the foregoing Example 1, there are reacted 2.45 g (0.025 mol) of imidazolin-2-thione with 6.96 g (0.05 mol) of decahydroquinoline and 1.5 g (0.05 mol) of formaldehyde. The reaction temperature is 80° C., duration—1.5–2 hours. The desired product yield is 8.9 g which corresponds to 89% of the theoretical value.

EXAMPLE 8

N,N'-bis-(decahydroquinolino-N-methyl)-imidazolin-2-thione

Under conditions similar to those of Example 1 hereinbefore, reacted are 2,45 g (0.025 mol) of imidazolin-2-thione with 6.96 g (0.05 mol) of decahydroquinoline and 1.5 g (0.05 mol) of formaldehyde. The reaction medium is distilled water. The reaction temperature is 55° to 60° C., duration—1.5–2 hours. The desired product yield is 8.7 g which corresponds to 86% of the theoretical value.

EXAMPLE 9

N,N'-bis-(decahydroquinolino-N-methyl)-imidazolin-2-thione

Under conditions similar to those described in the foregoing Example 1, there are reacted 2.45 g (0.025 mol) of imidazolin-2-thione with 6.96 g (0.05 mol) of decahydroquinoline and 1.5 g (0.05 mol) of formaldehyde. The reaction medium is dioxane. The reaction temperature is 55°–60° C., duration—1.5–2 hours. The desired product yield is 9.28 g which corresponds to 92.5% of the theoretical value.

EXAMPLE 10

N,N'-bis-(decahydroquinolino-N-methyl)-imidazolin-2-thione

Under conditions similar to those described in the foregoing Example 1, reacted are 2.45 g (0.025 mol) of imidazolin-2-thione with 6.96 g (0.05 mol) of decahydroquinoline and 1.5 g (0.05 mol) of formaldehyde. As the reaction medium use is made of benzene. The reaction temperature is 55°–60° C., duration—1.5–2 hours. The desired product yield is 8.98 g which corresponds to 89.5% of the theoretical value.

What is claimed is:

1. N,N'-bis-substituted imidazolin-2-thiones of the formula:

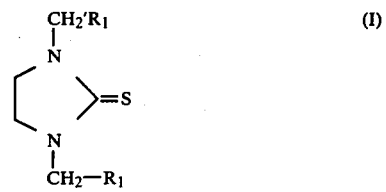

wherein
$R_1$ is

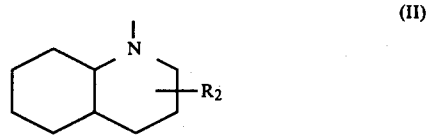

$R_2$ is hydrogen, methyl.

2. The thione of claim 1, wherein $R_1$ is decahydroquinoline.

3. The thione of claim 1, wherein $R_1$ is 2-methyl-decahydroquinoline.

4. The thione of claim 1, wherein $R_1$ is 4-methyl-decahydroquinoline.

5. The thione of claim 1, wherein $R_1$ is 6-methyl-decahydroquinoline.

6. The thione of claim 1, wherein $R_1$ is 8-methyl-decahydroquinoline.